United States Patent
Blischak et al.

(10) Patent No.: US 7,840,268 B2
(45) Date of Patent: Nov. 23, 2010

(54) SYSTEM AND METHOD OF MANAGING MEDICAL DEVICE HISTORICAL DATA

(75) Inventors: Brian R. Blischak, Allen, TX (US); Roger J. Hill, Richardson, TX (US); Robert L. McCormick, Jr., Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 960 days.

(21) Appl. No.: 11/157,023

(22) Filed: Jun. 20, 2005

(65) Prior Publication Data

US 2005/0283210 A1    Dec. 22, 2005

Related U.S. Application Data

(60) Provisional application No. 60/581,434, filed on Jun. 21, 2004.

(51) Int. Cl.
    *A61N 1/08*    (2006.01)
(52) U.S. Cl. ............... 607/31; 607/30; 607/32; 607/59; 607/63
(58) Field of Classification Search ............. 607/30–32, 607/59, 63
    See application file for complete search history.

(56) References Cited

U.S. PATENT DOCUMENTS

| | | | |
|---|---|---|---|
| 5,513,645 A | 5/1996 | Jacobson et al. | |
| 5,722,999 A | 3/1998 | Snell | |
| 5,836,989 A * | 11/1998 | Shelton | 607/27 |
| 5,938,690 A | 8/1999 | Law et al. | |
| 6,027,456 A | 2/2000 | Feler et al. | |
| 6,327,501 B1 | 12/2001 | Levine et al. | |
| 6,347,329 B1 * | 2/2002 | Evans | 709/202 |
| 6,609,031 B1 | 8/2003 | Law et al. | |
| 6,620,151 B2 | 9/2003 | Blischak et al. | |
| 2002/0115939 A1 | 8/2002 | Mulligan et al. | |
| 2003/0065370 A1 | 4/2003 | Lebel et al. | |

OTHER PUBLICATIONS

European Search Report Issued for EP 05 25 3836 dated Sep. 26, 2005.
Medtronic, "SYNCHROMED® II, Programmable Infusion System Clinical Reference Guide, Programming," pp. 14-16, Apr. 2004.

* cited by examiner

*Primary Examiner*—Carl H Layno
*Assistant Examiner*—Natasha N Patel
(74) *Attorney, Agent, or Firm*—Christopher S. L. Crawford; Peter Lando; Melissa Acosta

(57) ABSTRACT

Disclosed are systems and methods which provide management of historical information associated with a medical device, such as an implantable neurostimulation pulse generator, drug pump, cardiac device, hearing enhancement device, or vision enhancement device. Such management of historical information includes storage of historical information within an associated medical device. Historical information stored within a medical device may provide a complete summary of the use, configuration, and operation of the medical device, e.g., information spanning the entire in-service life of the medical device. Historical information for which management is provided may include both static data and dynamic data. The historical information may be used in configuring the medical device, analyzing the operation of the medical device, autonomously altering operation of the medical device, etcetera.

5 Claims, 3 Drawing Sheets

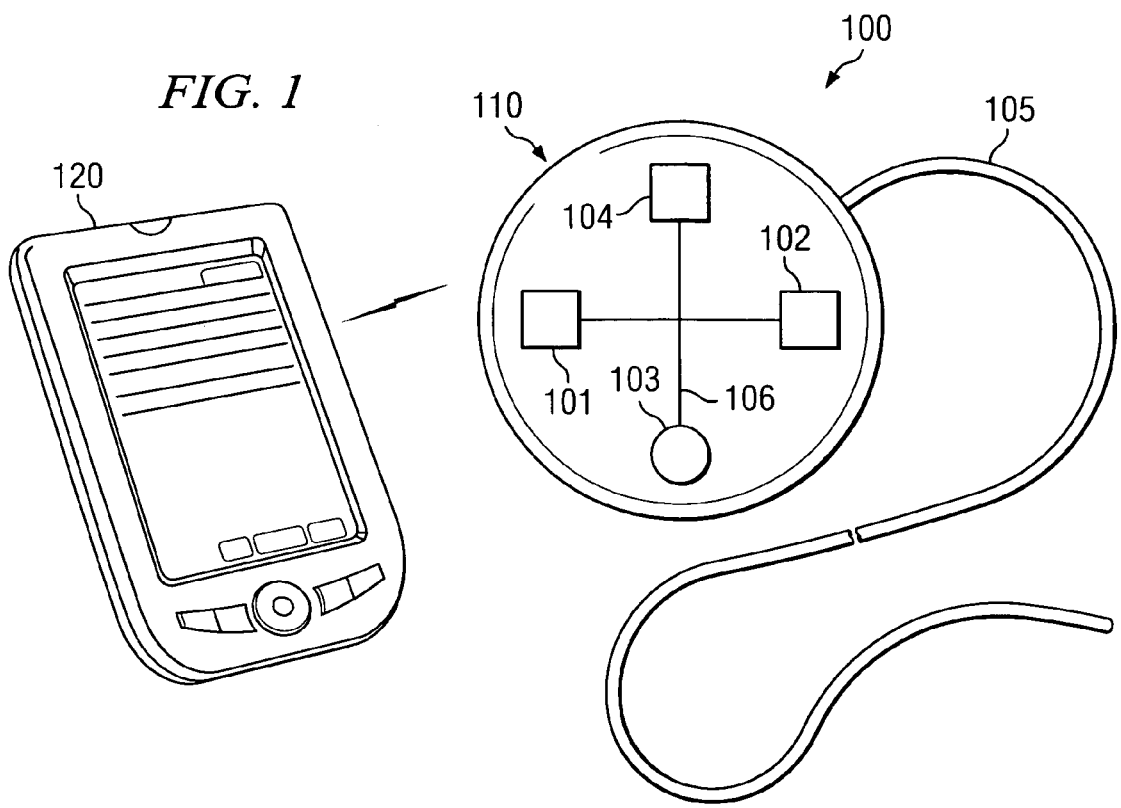

SYSTEM AND METHOD OF MANAGING MEDICAL DEVICE HISTORICAL DATA

CROSS-REFERENCE TO RELATED APPLICATIONS

The present application claims priority to co-pending U.S. Provisional Patent Application Ser. No. 60/581,434 entitled "System and Method of Managing Medical Device Historical Data," filed Jun. 21, 2004, the disclosure of which is hereby incorporated herein by reference. The present application is related to co-pending and commonly assigned U.S. patent application Ser. No. 11/060,241 entitled "Reduced Size Programmable Drug Pump," filed Feb. 17, 2005, and U.S. Provisional Patent Application Ser. No. 60/581,516 entitled "Reduced Size Programmable Drug Pump," file Jun. 21, 2004, the disclosures of which are hereby incorporated herein by reference.

TECHNICAL FIELD

The invention relates generally to the management of historical data and, more particularly, to the management of historical data associated with the use of a medical device.

BACKGROUND OF THE INVENTION

Numerous medical devices have been developed and utilized for providing various therapies to patients, including systems for the management of pain through neurostimulation or localized drug delivery. For example, U.S. Pat. Nos. 5,938,690, 6,027,456, and 6,609,031, the disclosures of which are incorporated herein by reference, show neurostimulation systems in which a pulse generator and electrical lead are implanted in a patient to provide pain management through controlled electro stimulation. As another example, U.S. Pat. No. 6,620,151, the disclosure of which is incorporated herein by reference, shows a localized drug delivery system in which a drug pump and catheter are implanted in a patient to provide pain management through controlled delivery of an infusate to selected tissue. Such systems may be employed for purposes other than pain management, such as to provide continuous controlled delivery of an agent such as insulin for diabetes or baclofen for spasticity.

The foregoing implanted medial devices may provide a therapy regimen according to control parameters configured by a physician, nurse, or other clinician (referred to herein collectively as clinicians). For example, a clinician may configure a stimulation program setting forth electronic pulse frequency, amplitude, and electrode polarity for delivering a prescribed therapy using an implantable neurostimulation pulse generator. Similarly, a clinician may configure an infusate flow rate, flow pattern, and bolus size, lockout, and limit for delivering a prescribed therapy using an implantable drug pump. One or more of the foregoing control parameters may be input into a control system of the medical device in order to implement the prescribed therapy. Control parameters for implementing the foregoing may be input into a clinician programmer and downloaded to the patient's medical device.

Typically the clinician would record such control parameters and other patient relevant information, e.g., the type and concentration of infusate used, negative and/or positive responses to various therapies, maximum electronic pulse stimulation amplitudes, etcetera, in the patient's chart for later reference. Some medical device programmers may facilitate the clinician's updating a patient chart by providing a hardcopy output of the current control parameter settings. Such a hardcopy report may be affixed to the patient's chart along with other relevant information, such as handwritten notations, medical transcripts, lab results, x-ray images, etcetera, to provide a relatively complete record of the patient's therapy for later reference when monitoring, adjusting, or changing the therapy regimen. Additionally, some device programmers may retain a copy of the last set of control parameters (currently downloaded control parameters) associated with a patient device programmed using that device programmer.

Periodically, such as in response to patient feedback, in response to patient events, throughout the course of a trial period, etcetera, the clinician may adjust one or more of the foregoing control parameters. Accordingly, the clinician may review the patient's chart for information with respect to the current control parameter settings, and perhaps any previously implemented control parameter settings. The clinician may then adjust the medical device control parameters using a clinician programmer to download new control parameters to the patient's medical device in order to provide a revised therapy, and again update the patient's chart for later reference.

The above described clinician review and updating of patient chart information is often time consuming and inconvenient. For example, it may be difficult for a clinician to efficiently glean information regarding a series of control parameter settings and their therapeutic effects as reported by the patient in order to determine a next control parameter set to implement. Further complicating the clinician's obtaining the needed information from such charts is the fact that many such clinicians may be serving many patients relatively quickly throughout the day. Additionally, several different clinicians, such as those of a particular clinic, may consult with a patient over the course of the patient's therapy, resulting in useful information being stored in a currently unavailable location (e.g., a clinician programmer used by a different clinician) and/or variations in the particular information recorded in the chart and in the way the information is presented and formatted. For example, portions of a patient's data may be stored on each of several clinician programmers in a single clinic, or the clinic may be forced to implement a procedure wherein only a specific clinician programmer is used for a particular patient. A patient may travel or present him/herself at an emergency room where the patient's information may be unavailable.

Accordingly, there is a need in the art for improved techniques for managing medical device historical data. Additionally, there is a need in the art for management of medical device historical data which efficiently presents such information in a manner easily assimilated by a particular individual having a need for the data. There is a further need in the art for medical device historical data to be readily and conveniently available when needed.

BRIEF SUMMARY OF THE INVENTION

The present invention is directed to systems and methods which provide management of historical information associated with a medical device, such as an implantable neurostimulation pulse generator, hearing enhancement device, vision enhancement device, cardiac device, drug pump, etcetera. Management of historical information according to the present invention includes storage of historical information within an associated medical device. For example, embodiments of the invention operate to make historical data associated with the use and operation of a medical device readily and conveniently available, such as during clinician interaction (e.g., monitoring and programming), by keeping such information with the medical device itself. Accordingly, irrespective of a particular clinician working with the patient and their associated medical device and irrespective of an external telemetry device used, that clinician may be provided access to useful historical information even without access to a patient's medical chart or other file. Historical information stored within a medical device according to embodiments of the invention eliminates or mitigates issues with respect to synchronizing patient data. For example, by storing the appropriate historical information within the patient's medical device, a clinician may be assured of having a complete and up-to-date set of the relevant patient data available when interacting with the patient, without having to worry about obtaining data from multiple sources or dealing with duplicate data entries.

Historical information stored within a medical device according to embodiments of the invention may provide a complete summary of the use, configuration, and operation of the medical device, e.g., information spanning up to the entire in-service life of the medical device. Embodiments of the present invention provide for storage of historical information such as the original factory calibration settings for the device, information with respect to accessories coupled thereto (e.g., the model number of a catheter or lead, the length of a catheter or lead, the impedance of electrodes, the flow rate provided by a catheter, etcetera), the date of implantation, records of each time configuration settings or a medical device program was changed, records of each time a user makes particular requests or changes (e.g., increases a stimulation amplitude, requests a bolus, etcetera), information with respect to predefined limits having been reached (e.g., a maximum bolus limit has been reached, a minimum infusate reservoir or power supply capacity has been reached, etcetera), records of alarms triggered (e.g., low power supply, low infusate, maximum time between service, etcetera), records of periodic service (e.g., infusate refill, change in drug concentration, program change, stimulation set change, etcetera), records of maintenance procedures (e.g., flushing, back-flushing, etcetera), and/or the like.

Embodiments of the invention may store historical information in addition to or in the alternative to medical device operating parameters and operational history. For example, historical information stored within a medical device adapted according to the present invention may include notes, such as clinician notes providing a record as to why particular control parameters were changed, what results have been achieved and/or are trying to be achieved, a patient's reaction to past therapy settings, etcetera.

Historical information stored by a medical device according to embodiments of the invention may include data which is actively stored to the device, such as control parameters and notes, as well as data which is collected during operation, such as operating requests made by patients (e.g., operating adjustments, bolus requests) and limits or lockouts reached (e.g., denial of a bolus request as having reached a daily maximum). A clinician may use such information, perhaps through downloading the historical information to a clinician programmer during an office visit, not only to obtain information that might otherwise require review of a patient chart, but also to gain insight into the patient and the patient's use of the medical device. Accordingly, historical information managed according to embodiments of the present invention may provide valuable information with respect to how a therapy should be modified.

Historical information stored according to embodiments of the present invention is stored in a medical device as raw data, e.g., data as monitored by, collected by, or provided to the medical device which remains substantially unprocessed by the medical device. However, this information is preferably stored in a defined data structure, or perhaps a self describing format (e.g., extensible markup language (XML)), to facilitate retrieval and use of the data by external systems, such as a clinician programmer. For example, a clinician programmer, such as may be provided in the form of a handheld computing device (e.g., the IPAQ™ series of handheld computers available from Hewlett Packard Company or the PALM™ series of handheld computers available from PalmOne, Inc.) having appropriate programming and a suitable interface may be utilized in monitoring and programming a medical device implanted in a patient. Such a clinician programmer may query, or otherwise be provided raw data comprising the historical information for a medical device and present that information to the clinician in a variety of formats. For example, embodiments of the invention provide data processing within a clinician programmer to process historical information and present reports, perhaps in a graphical or tabular format, to a clinician.

According to embodiments of the invention, historical information may be processed, or otherwise utilized, by a medical device in which it is stored to provide desired operation. For example, a control system within an implanted pulse generator or drug pump may analyze historical information to determine that a patient repetitively alters a control parameter at a particular time of day. The control system may use this historical information to automatically adjust such a parameter, perhaps within preset guidelines closely controlling the autonomous operation of such a device, to provide the desired effect without the patient having to manually make the adjustment. Alternatively, the control system may use this historical information to alert the clinician to the existence of this problem, so that the clinician can use his clinical judgment to determine what, if any, adjustment should be made.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIG. 1 shows a system adapted according to embodiments of the present invention;

FIG. 2 shows historical information as may be managed according to embodiments of the present invention;

DETAILED DESCRIPTION OF THE INVENTION

Figure 3:
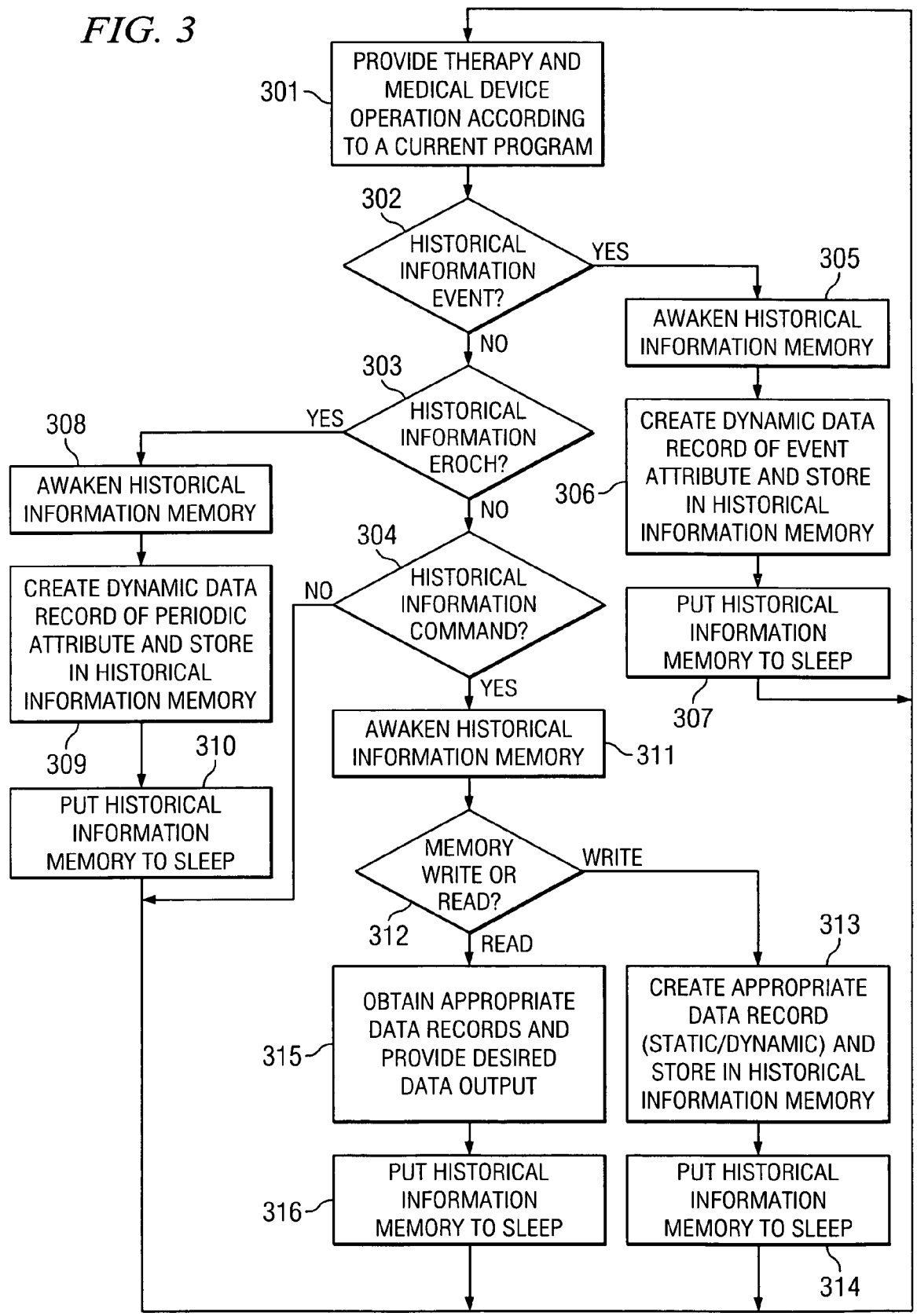
FIG. 3 shows a flow diagram of operation of a medical device according to embodiments of the present invention.

Directing attention to FIG. 1, system 100 is shown adapted according to an embodiment of the present invention. System 100 of the illustrated embodiment includes medical device 110, such as may comprise an implantable pulse generator or a neurostimulation system, an implantable drug pump of a localized drug delivery system, an implantable cardiac device (e.g., a pace maker or defibrillator) used in cardiac therapy, an implantable hearing enhancement device (e.g., cochlear implant) used in aural therapy, or an implantable vision enhancement device used in sight therapy, in wireless communication with external clinician programmer 120.

Medical device 110 of the illustrated embodiment is coupled to conduit 105, such as may comprise an electronic lead where medical device 110 comprises an implantable pulse generator or a catheter where medical device 110 comprises a drug pump, to deliver therapeutic stimulus. Medical device 110 and its attendant conduit 105 may be implanted within the body of a host patient for which therapy is to be provided.

Medical device 110 of the illustrated embodiment includes various functional modules disposed therein. The illustrated embodiment of medical device 110 includes historical information memory 101, controller 102, power supply 103, and other services module 104 shown here coupled by bus 106.

Historical information memory 101 provides storage of historical information of the present invention as described in further detail below. Although shown separate from other functional modules of medical device 110, historical information memory 101 may be integral with one or more such functional module, such as may comprise internal memory of a processor device of controller 102. Historical information memory 101 of a preferred embodiment provides sufficient storage capacity for storing historical information for the service live of medical device 100 while presenting a size and form factor easily integratable into medical device 100 without introducing undesired space and/or size issues with respect to medical device 110. Of course, embodiments of the invention may implement a historical information memory of any capacity, size, and/or form factor determined suitable for a particular situation. Additionally or alternatively, multiple memory modules may be implemented, such as in a cascaded architecture, according to embodiments of the invention. According to one embodiment, multiple memory modules may be implemented which provide a segmented historical information memory. For example, a first memory module may provide encrypted storage of prescription information and clinician notes while a second memory module may provide un-encrypted storage of event attributes, patient information, etcetera.

It should be appreciated that the amount of storage capacity utilized in storage of historical information for the life of a medical device depends upon the number of records to be kept (e.g., the number of different events and parameters stored) as well as the amount of data in each record (e.g., resolution used for time stamps, amount of information stored for each event, etcetera). A preferred embodiment historical information memory comprises a 256 kilobyte memory to store approximately 10,000 records, containing information as described in further detail below, which is believed to provide sufficient capacity for storage of historical information for the life of a medical device, such as an implantable drug pump or an implantable pulse generator.

Historical information memory 101 may employ any of a number of memory technologies, now known or later to be developed, in providing storage of historical information according to the present invention. For example, historical information memory 101 may comprise one or more of random access memory (RAM), read only memory (ROM), programmable read only memory (PROM), erasable programmable read only memory (EPROM), electrically erasable programmable read only memory (EEPROM), flash memory, magnetic memory, optical memory, bubble memory, molecular memory, and the like.

According to embodiments of the invention, historical information memory 101 is provided in a configuration in which power is not consumed to retain the historical information, although power is consumed in historical information memory read/write operations. Accordingly, historical information memory 101 may comprise flash memory to present a memory resource which consumes little power when reading or writing data to the memory and which consumes little or no power for non-volatile storage of data. Preferred embodiments of the present invention operate to power-up historical information memory 101 substantially only when reading from or writing to the memory, thereby conserving power which may be provided from a limited supply such as power supply 103. Accordingly, although functional blocks, such as controller 102 and/or other services module 104 may be powered-up for much or all the service life of medical device 110, historical information memory 101 may be powered-up only during limited times, such as when control parameters are changed in order to store previous settings in the historical information memory, when an event such as maximum bolus or low power supply is detected and that information is stored in the historical information memory, etcetera.

It should be appreciated that historical information may not comprise all the data stored within or by medical device 100. For example, active or current control parameters or modes etcetera may be stored within medical device 100 to provide desired operation thereof. Such currently active data may be stored within a portion of historical information memory 101, if desired. For example, historical information memory 101 may comprise a memory stack wherein the information at the top of the stack provides current control parameters and the information further down in the stack provides a history of control parameters implemented with respect to medical device 100. However, embodiments of the present invention provide a memory structure in which currently active data is held in a non-volatile memory, preferably with error checking etcetera, which provides relatively fast access, whereas historical information is held in a low power, perhaps slower access, non-volatile memory. The historical information memory may provide some level of error checking, such as through use of parity bits, but may implement less fault tolerant and/or non-redundant data storage techniques than used with respect to currently active data, such as because the historical data may be less critical to patient safety. Of course, embodiments of the invention may implement any level of fault tolerance and/or data redundancy, such as to implement error checking and/or error correction algorithms with respect to historical information, although such techniques are expected to present a more complex and higher power consuming memory structure.

Controller 102 may comprise a processor-based system, such as may include a central processing unit (CPU), memory, and an instruction set (e.g., software) defining operation as set forth herein, controlling various operational aspects of controller 102. For example, controller 102 may provide a prescribed therapy through controlling delivery of therapeutic stimulus via conduit 105 in accordance with a current set of control parameters provided thereto by a clinician. Controller 102 may interact with other functional modules of medical device 110 in providing desired operations, such as the aforementioned prescribed therapy or in providing storage and retrieval of historical information in historical memory 101, communicating with clinician programmer 120 such as using communication interfaces and/or encryption protocols provided by other services module 104, etcetera. Embodiments of controller 102 may comprise a plurality of controller functions (e.g., separate and/or independent controllers), such as to provide a main system controller (e.g., to provide primary control of medical device 110) and a historical information memory controller (e.g., to provide access control with respect to historical information memory 101).

Power supply 103 preferably provides a source of energy for powering one or more functional modules, such as historical information memory 101, controller 102, and other services module 104. Power supply 103 may be rechargeable and may implement any of a number of battery, or other renewable energy supply, technologies now known or later developed. Because historical information memory 101 of a preferred embodiment does not consume power to retain the historical information, power supply 103 of embodiments may comprise a coil for inductively coupling with an external power supply to provide power as needed (e.g., during historical information memory read/write operations). Power supply 103 of embodiments additionally or alternatively comprises a battery, a capacitor, a super-capacitor, a micropower generator, or other energy reservoir to provide power, at least temporarily, independent of the availability of an external power supply.

Other services module 104 may provide one or more functions useful in operation of medical device 110. For example, other service module 104 may provide a communication interface, such as may provide wireless communication protocols for establishing communication between medical device 110 and clinician programmer 120. Wireless communications supported by other service module 104 may include proprietary protocols (e.g., proprietary radio frequency (RF) protocols) and/or standardized protocols (e.g., Bluetooth, IEEE 802.11, IEEE 802.16, general packet radio service (GPRS), etcetera). Other services module 104 may provide cryptographic functions, such as symmetric (e.g., private key) and/or asymmetric (e.g., public key) cryptography, useful in preventing unauthorized interception of information communicated between medical device 110 and clinician programmer 120 or otherwise preventing unauthorized access to information within medical device 110. Additionally or alternatively, other service module 104 may provide functions such as monitoring one or more aspect of operation of medical device 110, possibly providing data to controller 102 for analysis, use in controlling the medical device, storage in historical information memory 101, and/or the like. It should be appreciated that, although illustrated as a single functional block, other service module 104 of embodiments may comprise any number of functional elements.

Clinician programmer 120 of the illustrated embodiment comprises a general-purpose handheld computer, such as an IPAQ™ pocket personal computer available from Hewlett Packard Company, operable under control of an instruction set defining clinician programmer operation as described herein. Clinician programmer 120 of a preferred embodiment includes a wireless interface corresponding to that of medical device 110, e.g., as may be provided by other services module 104. For example, clinician programmer 120 may provide an interface for communicating with medical device which uses proprietary protocols (e.g., proprietary RF protocols) and/or which uses standardized protocols (e.g., Bluetooth, IEEE 802.11, IEEE 802.16, GPRS, etcetera).

Software operable upon clinician programmer 120 of embodiments of the invention provides a capability to upload data, such as updated or revised control parameters, operating programs, testing and diagnostic sequences, etcetera, to medical device 110 as well as a capability to download data, such as current control parameters, status information, historical information, testing and diagnostic results, etcetera, from medical device 110. Moreover, software operable upon clinician programmer 120 of preferred embodiments provides data processing functionality, such as to facilitate a clinician assimilating data obtained from medical device 110 and/or to facilitate a clinician controlling/programming medical device 110. According to preferred embodiments, software operable upon clinician programmer 120 facilitates exporting data, such as may comprise historical information, to an external system, such as a computer or computer network, for archiving, further analysis, charting, printing, etcetera.

Having described a medical device architecture and associated clinician programmer, each adapted according to an embodiment of the invention, historical information which may be managed according to embodiments of the invention shall be described. Historical information managed according to embodiments of the present invention includes a plurality of data types. For example, as shown in the table of FIG. 2, which represents an embodiment of historical information as may be stored in historical information memory 101, historical information may include static data 210 and dynamic data 220.

Static data 210 may include information with respect to medical device 110, the patient, the therapy being provided, a clinician primarily responsible with respect to the medical device and/or patient, etcetera. For example, static data 210 of the illustrated embodiment includes patient identification information 211, such as may comprise a patient's name, social security number, clinician assigned patient identification number, address, phone number, insurance information, and/or the like. Information with respect to the patient may be particularly useful in a clinician verifying that correct corresponding information, such as a paper chart, is being referred to and/or that information extracted from or input to the medical device is associated with the correct patient. The illustrated embodiment of static data 210 further includes in-service data 212 providing information with respect to the date medical device 110 was put into service, the model of the medical device, factory calibration settings, options or features provided or enabled with respect to the medical device, and/or the like. Such information may be particularly useful in determining the remaining service life of medical device 110, determining dates for particular events such as maintenance, configuring control parameters and programs, etcetera. Static data 210 of the illustrated embodiment further includes conduit particulars, such as may include the model and/or length of a catheter used with an implantable drug pump, the number and impedance of electrodes used with an implantable pulse generator, etcetera. Such information may be particularly useful with respect to a clinician and/or software of clinician programmer 120 determining appropriate control parameter settings, how long a change in drug concentration in the infusate will require to take effect, etcetera.

Although several examples of static data are provided in FIG. 2, it should be appreciated that data in addition to or in the alternative to that shown may be included as static data according to embodiments of the invention. For example, a list of the particular drugs that could be administered by the drug pump (e.g., to facilitate consistency in data entry), a particular drug comprising the infusate of a drug pump, the volume of infusate held by a catheter, the delivery mode and associated parameters of a drug pump, clinician imposed limits on patient alterable aspects of the medical device (e.g., maximum bolus, maximum stimulation amplitude, etcetera), clinician imposed limits for operation of the medical device (e.g., maximum does, drug allergies, etcetera), operational preferences (e.g., whether alarms are active, maximum dose limits, alarming methods, etcetera), and/or the like may be stored as historical information.

Dynamic data 220 may include information with respect to control and operation of medical device 110, alarm and status conditions of medical device 110, the therapy being provided, user (e.g., patient and clinician) interaction with medical device 110, the identity of a clinician accessing/making adjustments to the medical device, etcetera. Because various data may be included as dynamic data, embodiments of the invention may utilize data identification information useful in identifying the particular data stored in a dynamic data record. Moreover, due to the dynamic nature of this data, dynamic data 220 preferably includes temporal information. Accordingly, dynamic data of the illustrated embodiment is provided in records including a plurality of fields. For example, dynamic data records 221-223 of the illustrated embodiment each include a time stamp (time stamp fields 221a-223a, respectively), a data identifier (data identifier fields 221b-223b, respectively), and a data field (data fields 221c-223c).

As discussed above, dynamic data 220 of embodiments of the invention may include various data, such as associated with particular events, controls, operation, etcetera. For example, dynamic data 220 of the illustrated embodiment includes dynamic data record 221 which includes data field 221c denoting a particular drug, here morphine, was added to medical device 110, as indicated by the "refill" entry in data identifier field 221b, at the date and time logged in time stamp field 221a. Dynamic data record 222 includes data field 222c denoting that a patient was allowed a bolus request, as indicated by the "bolus" entry in data identifier field 222b, at the date and time logged in time stamp field 222a. Dynamic data record 223 includes data field 223c providing a drug reservoir pressure reading, as indicated by the "pressure sensor" entry in data identifier field 223b, at the date and time logged in time stamp field 223a.

Although several examples of dynamic data are provided in FIG. 2, it should be appreciated that data in addition to or in the alternative to that shown may be included as dynamic data according to embodiments of the invention. For example, information with respect to a drug concentration in the infusate of a drug pump may be stored as historical information.

It should be appreciated that the type, amount, and resolution of data stored may affect the capacity of historical information memory 101 consumed by the various data records. For example, time stamp information may be stored which indicates a particular day, a particular hour, a particular minute, or even a particular second. However, the more resolution provided by the time stamp, the more memory capacity consumed by that information. For example, a time stamp providing information with respect to a particular second (e.g., day/month/year/hour/minute/second) an event occurred may consume 4 bytes of capacity, whereas a time stamp providing information with respect to a particular hour (e.g., day/month/year/hour) may consume 3 bytes of capacity. It is expected that the dynamic data attributes stored, along with their associated data identifiers, may consume on the order of 6 bytes of capacity according to embodiments of the invention. Much of the static data stored according to embodiments of the invention may be stored using a similar amount of capacity. Of course, some data, such as clinician notes, patient identification, etcetera, may consume appreciably more capacity, such as on the order of 25-100 bytes. However, it is expected that such entries will be relatively few and therefore will not present a significant impact on historical information memory utilization. Embodiments of the invention may establish maximum sizes with respect to any or all the data elements stored by historical information memory 101.

Embodiments of the invention provide efficient storage of historical information by implementing memory conservation techniques such as selecting a data resolution appropriate to the particular data stored, utilizing data codes to represent reoccurring data, implementing data compression techniques, and/or the like. For example, although dynamic data stored in a medical device which has an operational life expectancy of several years will generally benefit from a time stamp resolution which at least provides indication of a particular day, not all such data will benefit from time stamp resolution to the second. Accordingly, particular dynamic data which is particularly time sensitive, such as monitored events, may be provided a time stamp with higher resolution (e.g., to the second) whereas other dynamic data which is not particularly time sensitive, such as clinician notes, may be provided a time stamp with lower resolution (e.g., to the day). Additionally or alternatively, various pieces of data may be stored efficiently using codes, such as a short numerical sequence to represent otherwise lengthy phrases such as "refill," "bolus," and "pressure sensor" shown above.

The data stored in historical memory 101 may be stored in response to an event, periodically, at the command of a user, etcetera. For example, a clinician accessing an implantable drug pump comprising medical device 110 in order to replenish an infusate supply may cause a dynamic data record such as dynamic data record 221 to be automatically created and stored to historical information memory 101. Similarly, a patient activating a bolus delivery control may cause a dynamic data record such as dynamic data record 222 to be automatically created and stored to historical information memory 101. In contrast, dynamic data records such as dynamic data record 223 may be created and stored to historical information memory 101 periodically, such as under control of an operating program of medical device 110, to provide an operational "snapshot" and/or to facilitate monitoring/analyzing attributes over time (e.g., a series of such snapshots are taken to show pressure fluctuation over time, power supply drain versus time, etcetera). Although not shown in FIG. 2, dynamic data 220 may include data records created and stored responsive to an event, such as a power supply capacity dropping below a predetermined threshold, an infusate reservoir level dropping below a predetermined level, a patient reaching a bolus limit, a temperature exceeding a predetermined maximum, etcetera. Dynamic data 220 may include clinician notes (not shown) stored at the command of a clinician. Likewise, data of static data 210 may have been stored at the command of a clinician.

As discussed above, historical information may be created and stored in historical information memory 101 in a number of ways. Likewise, the information may be retrieved and/or used in a number of ways according to embodiments of the invention. Several illustrative examples of creation and storage of historical information as well as retrieval and use of historical information are provided in the flow diagrams of FIGS. 3 and 4 below.

Referring to FIG. 3, a flow diagram of operation of medical device 110 accessing historical information memory 101 to create data records and retrieve data is shown according to one embodiment. In the illustrated flow diagram, medical device 110 provides therapy and operation, e.g., provides infusate delivery or neurostimulation, according to a current program at block 301.

At block 302 a determination is made with respect to whether a historical information event has occurred. For example, an infusate reservoir may have dropped below a predetermined minimum level, a power supply capacity may have dropped below a predetermined level, a reservoir pressure or temperature may have reached a threshold value, etcetera. If it is determined at block 302 that a historical information event has occurred, the flow proceeds to block 305 where historical information memory 101 is awakened. Thereafter, at block 306 a dynamic data record is created, such as may include event attribute data (e.g., a monitored level or other attribute) as well as related data (e.g., a time stamp, a data identifier, etcetera), and stored in historical information memory 101. At block 307 historical information memory 101 is again put in a sleep mode and processing returns to block 301.

If, at block 302, it is determined that a historical information event has not occurred, processing proceeds to block 303. At block 303 a determination is made with respect to whether a historical information epoch has occurred. For example, a time period for taking an operational "snapshot" may have transpired. Such an epoch may be on the order of seconds, minutes, days, months, etcetera. If it is determined at block 303 that a historical information epoch has occurred, the flow proceeds to block 308 where historical information memory 101 is awakened. Thereafter, at block 309 a dynamic data record is created, such as may include periodically monitored data (e.g., a sensor input or other status) as well as related data (e.g., a time stamp, a data identifier, etcetera), and stored in historical information memory 101. At block 310 historical information memory 101 is again put in a sleep mode and processing returns to block 301.

If, at block 303, it is determined that a historical information epoch has not occurred, processing proceeds to block 304. At block 304 a determination is made with respect to whether a historical information command has been invoked. For example, a user may provide a command for reading from or writing to historical information memory 101. Additionally or alternatively, a historical information command may be invoked by an operational function, such as controller 102, other services module 104, clinician programmer 120, and/or the like. If it is determined at block 304 that a historical information command has been invoked, the flow proceeds to block 311 where historical information memory 101 is awakened. Thereafter, at block 312 a determination is made with respect to whether the historical information command is directed to a memory read or a memory write.

If, at block 312, it is determined that the historical information command is directed to a memory write, processing proceeds to block 313 where a dynamic data record is created, such as may include static and/or dynamic data (e.g., settings, control parameters, notes, etcetera) as well as related data (e.g., time stamp, data identifier, etcetera), and stored in historical information memory 101. At block 314 historical information memory 101 is again put in a sleep mode and processing returns to block 301.

If, at block 312, it is determined that the historical information command is directed to a memory read, processing proceeds to block 315 where appropriate data records are obtained from historical information memory 101 and output as requested. For example, a clinician accessing medical device 110 using clinician programmer 120 may request all or some of the historical information stored by historical information memory 101 in order to determine an appropriate change in therapy, to archive data in an external device containing records for multiple patients so that the experiences of this patient can be used to improve patient care for other patients, to confirm proper operation of medical device 110, to determine an expected remaining service live of medical device 110, etcetera. Additionally or alternatively, software of clinician programmer 120 may obtain all or some of the historical information stored by historical information memory 101 in order to present a report (perhaps graphical, tabular, and/or textual) showing a clinician operational attributes of medical device 110 over some period of time, to verify a clinician's current control parameter settings are within limits previously established with respect to medical device 110, to determine if a clinician's current control parameter settings have been previously implemented (e.g., to display relevant notes associated with such settings), etcetera. Likewise, functional modules of medical device 110 may access historical information, such as to adjust operation autonomously, to provide analysis and/or alarms, etcetera. For example, controller 102 may analyze historical information to determine that a patient increases stimulation amplitude each morning at approximately the same time, and thus adjust the stimulation amplitude of a pulse generator within allowed limits automatically for that patient during subsequent mornings at the appropriate time. After output of the historical information as requested at block 315, historical information memory 101 is again put in a sleep mode at block 316 and processing returns to block 301.

Although not expressly mentioned with respect to the operational flow described above, embodiments of the present invention may implement encryption and/or other security techniques with respect to the historical information. For example, any or all of blocks 306, 309, and 313 may operate to encrypt (e.g., using symmetric or asymmetric encryption techniques well known in the computer arts) some or all of the data record created and stored thereby. Additionally or alternatively, block 315 may operate to encrypt (e.g., using the aforementioned symmetric or asymmetric encryption techniques) some or all of the data before output thereof.

It should be appreciated that the above described operational flow is merely exemplary of operation according to embodiments of the invention. Alternative embodiments of the invention may provide one or more of the above described functions in an order different than that illustrated in FIG. 3. Likewise, embodiments of the invention may omit and/or add functions in providing an operational flow. For example, the memory awakening and sleep functions of blocks 305, 307, 308, 310, 311, 314, and 316 maybe omitted where historical information memory is continuously powered during such operation, such as where historical information memory is internal to controller 102. However, where flash memory or other memory power conservation techniques are used, such memory awakening and sleep functions may be desired.

Figure 4:
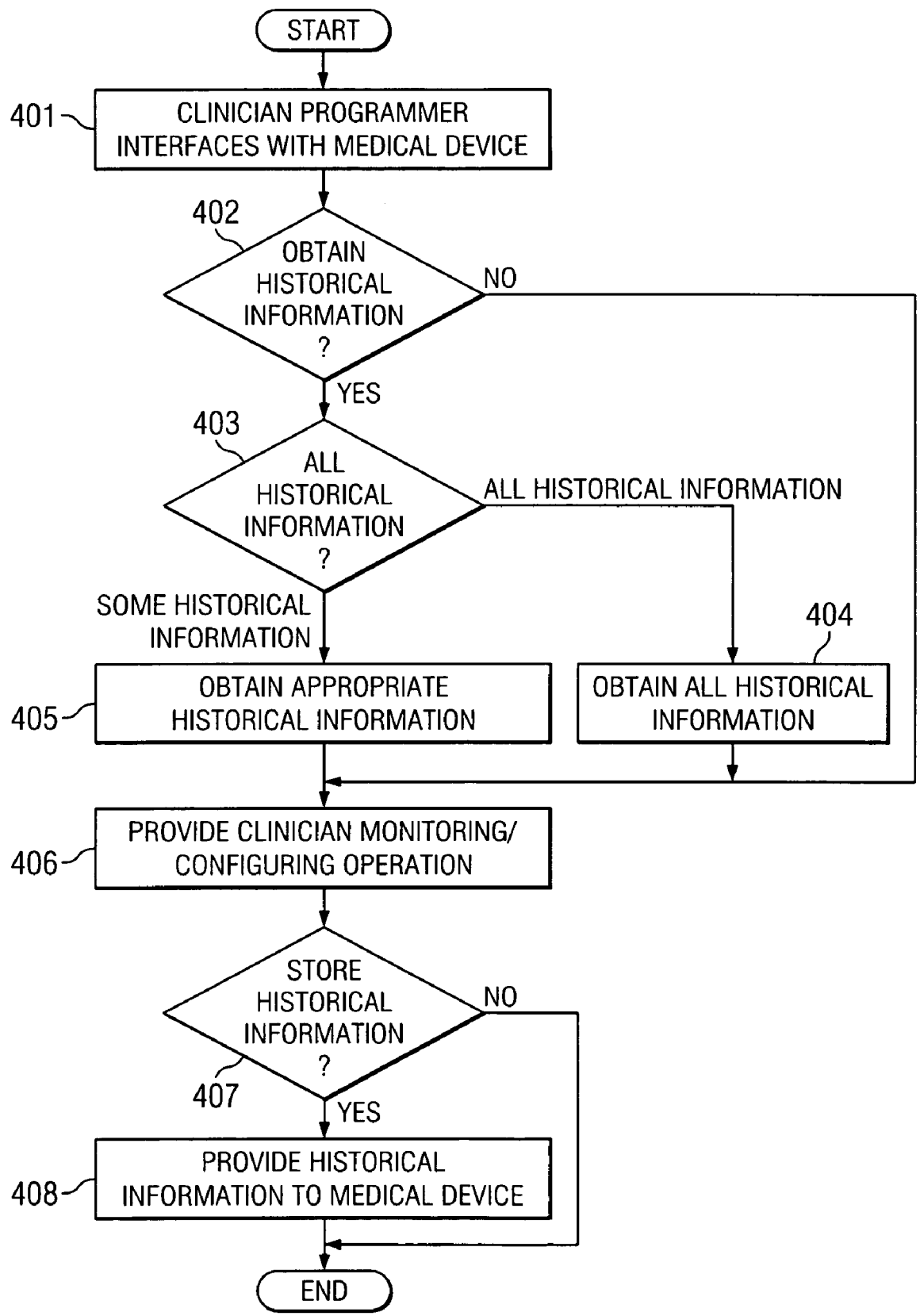
FIG. 4 shows a flow diagram of operation of a clinician programmer according to embodiments of the present invention.

Referring to FIG. 4, a flow diagram of operation of clinician programmer 120 accessing historical information of historical information memory 101 to facilitate clinician monitoring/configuring medical device 110 to create data records and retrieve data is shown according to one embodiment. In the illustrated flow diagram, clinician programmer 120 interfaces with medical device 110 at block 401. For example, at the beginning of a clinician visit with a patient, the clinician may hold an antenna coupled to (or integral with) clinician programmer 120 over a portion of (or in the vicinity of) the patient's body in which medical device 110 is implanted in order for the two devices to perform communication protocol handshaking and establish a data link there between. Embodiments of the invention may employ far field communications, such as may be established when medical device 110 is in a same area (e.g., room, building, or other communications area) as clinician programmer 120, or an antenna in communication therewith. A clinician may enter a code or other information identifying themselves as the ones accessing the medical device and/or making adjustments thereto.

At block 402 a determination is made by clinician programmer 120 as to whether historical information stored within historical information memory 101 of medical device 110 is to be obtained. For example, a clinician may be queried by software operating on clinician programmer 120 as to whether the clinician would like to obtain historical information from medical device 110. Additionally or alternatively, software operating on clinician programmer 120 may automatically determine if historical information is to be obtained, such as if a control parameter configuration mode is selected by a clinician in order to obtain past control parameter configuration settings.

If, at block 402, it is determined that historical information is not to be obtained, processing proceeds to block 406 wherein clinician monitoring/configuring operation is provided by clinician programmer 120. However, if it is determined that historical information is to be obtained at block 402, processing proceeds to block 403.

At block 403 a determination is made by clinician programmer 120 as to whether all historical information stored within historical information memory 101 of medical device 110 is to be obtained. It is expected that over the live of medical device 110 an appreciable amount of historical information will be compiled. Accordingly, transfer of all historical information from medical device 110 to clinician programmer 120 may consume an appreciable amount of time (e.g., more than 20 seconds). In situations where all historical information will not be used, it may be desirable to obtain a subset of the historical information (e.g., a particular type of historical information, historical information relevant to a particular window in time, historical information relevant to a particular event, etcetera) in order to avoid transmission delays and unnecessary drain of the power supply associated with transmission of a large amount of historical information which is not relevant to the present task.

If, at block 403, it is determined that all historical information is to be obtained, processing proceeds to block 404 wherein all historical information stored within historical information memory 101 is obtained and provided to clinician programmer 120. However, if it is determined that all historical information is not to be obtained at block 403, processing proceeds to block 405 wherein only a portion of the historical information stored within historical information memory 101 appropriate to the relevant task is obtained and provided to clinician programmer 120. The portion of historical information obtained may be selected through reference to a particular task or mode of operation selected by a user, reference to information input or otherwise selected by a user, a user response to a query, etcetera.

After obtaining historical information at either of blocks 404 and 405, processing according to the illustrated embodiment proceeds to block 406 wherein clinician monitoring/configuring operation is provided by clinician programmer 120. Clinician monitoring/configuring operation provided by clinician programmer 120 may utilize the historical information in any of a number of ways. For example, where a clinician is changing a concentration of drug in an infusate, historical information regarding the length of a catheter and/or the volume of the catheter may be used by software of clinician programmer 120 to calculate the period of delay associated with the new concentration reaching the delivery site. Where a clinician is changing infusate dosages, e.g., the flow rate, the bolus amount, the number of boluses allowed, etcetera, historical information regarding clinician selected daily maximum dosages may be used by software of clinician programmer 120 to determine if the new regimen would result in such maximum dosages being exceeded. Clinician programmer 120 may use historical information to generate a report for a clinician, such as to present a graphical representation of therapy stimulus delivered by medical device 110 over a previous period of time. The historical information may be particularly helpful to a clinician not otherwise familiar with the patient, such as a clinician treating the patient while the patient is on a trip, by providing not only detail with respect to the patient, but also history of the therapy implemented and clinician notes regarding the therapy. Similarly, such historical information may be useful in an emergency, such as through emergency room personnel obtaining telemetry from the medical device.

After clinician monitoring/configuring operation of block 406, processing according to the illustrated embodiment proceeds to block 407. At block 407 a determination is made as to whether historical information is to be stored within historical information memory 101. It may be determined automatically that historical information is to be stored when control parameters are changed, when a medical device operating program has been changed, etcetera, in order to store the previous settings and/or information with respect to the present changes. Additionally or alternatively, determinations with respect to storing historical information may be from user response to a query, such as indicating that notes are to be created and stored in medical device 110. It should be appreciated that storage of historical information as discussed herein may include nulling or deleting historical information. For example, a clinician may elect to delete some historical information entries, such as clinician notes or patient activations, but not to delete other historical information.

If no historical information is to be stored within historical information memory 101, processing according to the illustrated embodiment terminates. However, if historical information is to be stored within historical information memory 101, processing according to the illustrated embodiment proceeds to block 408.

At block 408 historical information is provided to medical device 110 by clinician programmer 120 for storage in historical information memory 101. Block 408 may provide operation to compile, collect, and/or solicit historical information to be stored, whether from a user or from other functions of clinician programmer 120. After operation of block 408 to provide historical information to medical device 110 for storage in historical information memory 101, processing according to the illustrated embodiment terminates.

It should be appreciated that operation of embodiments of the present invention provide advantages over prior art paper charts referred to by clinicians. For example, a clinician may select preferred formats for data to be presented in as well as the type of data of interest to him and historical information management techniques of the present invention may operate to retrieve the appropriate information from historical information management memory of a medical device and present the desired information in the appropriate format. Although the same data may be utilized by a number of different clinicians, it may be formatted or otherwise presented differently for each such clinician. Moreover, not only is the information made more readily available to the clinician, and in a format more easily assimilated by the clinician, but information heretofore otherwise unavailable, such as date and time of alarms and other events, history of patient operation and requests, snapshots of operating attributes, etcetera, are provided according to embodiments of the invention. Having historical information of embodiments of the invention stored in association with the medical device allows each different clinician which may work with a patient to have immediate access to the complete history. Moreover, the historical information may be utilized in providing a check with respect to control parameter adjustments or other changes made by a clinician prior to their being implemented by a medical device.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of operating a medical device system for providing a controllable therapy to a patient, the system comprising an implantable medical device and an external controller, the method comprising:

operating the implantable medical device, over a period of time, to provide a plurality of therapy regimes to the patient, each therapy regime being defined by one or more operational parameter values, the operational parameter values being communicated to the implantable medical device by the external controller;

storing and maintaining one or more prior operational parameter values for a respective therapy regime in a historical information memory of the implantable medical device upon communication of one or more new operational parameter values from the external controller;

storing and maintaining clinician notes in association with stored operational parameter values in the historical information memory of the implantable medical device; and operating the external controller to retrieve and display one or more clinician notes from the implantable medical device when input is received from a clinician to modify an operational parameter value to a value that substantially corresponds to a value that has been previously been utilized by the implantable medical device to provide a therapy regime to the patient.

2. The method of claim 1, further comprising:

periodically monitoring an operational attribute of said implantable medical device and said storing historical information in said historical information memory with respect to said periodically monitored operational attribute.

3. The method of claim 1, further comprising:

detecting a predetermined event and storing historical information in said memory stores information with respect to occurrence of said event.

4. The method of claim 1, further comprising:

automatically modifying an operational aspect of said implantable medical device as a function of said historical information.

5. The method of claim 1 further comprising:

varying a resolution of said temporal information as a function of a type of data provided in said record.

* * * * *